Figure 1:
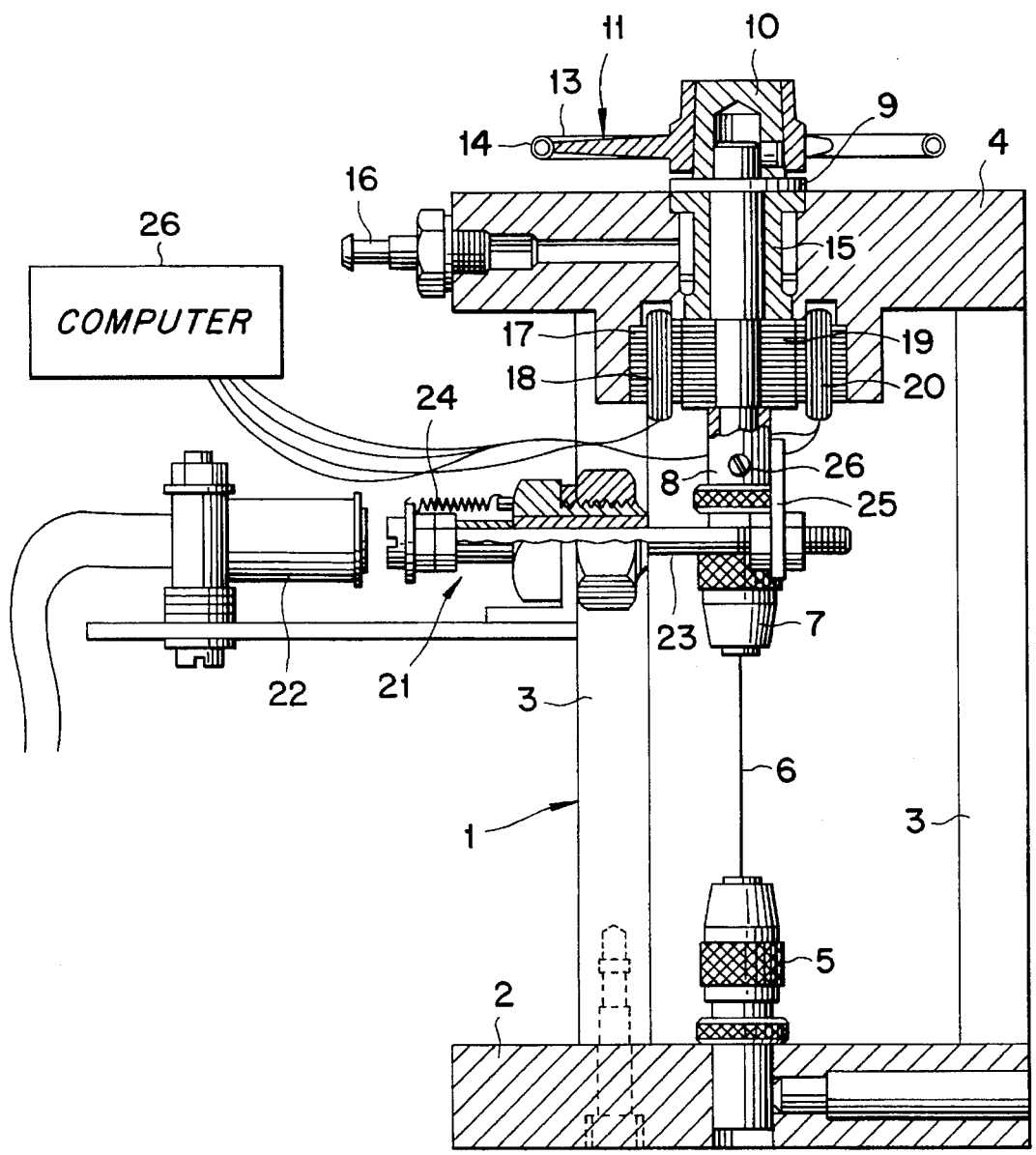

United States Patent [19]
Bohlin

[11] Patent Number: 5,565,620
[45] Date of Patent: Oct. 15, 1996

[54] METHOD FOR MEASURING RHEOLOGICAL PROPERTIES AND RHEOMETER FOR CARRYING OUT THE METHOD

[75] Inventor: Leif Bohlin, Sjöbo, Sweden

[73] Assignee: Aktiebolaget Medicinsk Reologi Lund, Lund, Sweden

[21] Appl. No.: 407,026

[22] PCT Filed: Oct. 5, 1993

[86] PCT No.: PCT/SE93/00801

§ 371 Date: Mar. 28, 1995

§ 102(e) Date: Mar. 28, 1995

[87] PCT Pub. No.: WO94/08222

PCT Pub. Date: Apr. 14, 1994

[30] Foreign Application Priority Data

Oct. 5, 1992 [SE] Sweden .................................. 9202915

[51] Int. Cl.$^6$ .............................. G01N 11/16; G01N 15/05
[52] U.S. Cl. ........................ 73/54.25; 73/54.26; 73/64.42; 73/61.65; 73/54.02
[58] Field of Search ............................ 73/54.02, 54.24, 73/54.25, 54.26, 54.27, 61.65, 64.42

[56] References Cited

U.S. PATENT DOCUMENTS

| | | | |
|---|---|---|---|
| 2,839,915 | 6/1958 | Roth et al. ........................... | 73/54.25 |
| 3,181,348 | 5/1965 | Lewis . | |
| 3,194,064 | 7/1965 | Miles ................................... | 73/54.24 |
| 4,026,671 | 5/1977 | Simons et al. ...................... | 73/54.25 |
| 4,154,093 | 5/1979 | Smith . | |
| 4,226,798 | 10/1980 | Cowfer et al. ...................... | 73/54.25 |
| 4,602,501 | 7/1986 | Hirata . | |
| 5,253,513 | 10/1993 | Van Arsdale et al. ............... | 73/54.02 |

FOREIGN PATENT DOCUMENTS

| | | | |
|---|---|---|---|
| 626304 | 8/1961 | Canada ................................ | 73/54.25 |
| 60-194330 | 10/1985 | Japan . | |
| 162129 | 6/1989 | Japan ................................... | 73/54.24 |
| 868474 | 9/1981 | U.S.S.R. .............................. | 73/54.25 |
| 1608498 | 11/1990 | U.S.S.R. .............................. | 73/54.24 |
| 810242 | 3/1959 | United Kingdom ................. | 73/54.25 |

OTHER PUBLICATIONS

Ashwin et al., "Viscometers Having Damped Torsional Oscillation", Journal of Scientific Instruments, vol. 37, Dec. 1960, pp. 480–485.

Berger et al., "A New Electromechanical Viscometer Designed For Biological Fluids", IEEE Transactions on Biomedical Engineering, vol. BME-25, No. 1, Jan. 1978, pp. 64–70.

Charles et al., "The Use of a Vibrating Wire Viscometer in Liquids", J. Phys. E: Sci. Instrum., vol. 13, No. 8, Aug. 1980, pp. 829–834.

"Viscosity Measurements Above 2000° C.", NBS Technical News Bulletin, vol. 412, No. 6, Jun. 1958, pp. 103–104.

*Primary Examiner*—Thomas P. Noland
*Assistant Examiner*—Daniel S. Larkin
*Attorney, Agent, or Firm*—Burns, Doane, Swecker & Mathis, L.L.P.

[57] ABSTRACT

In a method of measuring rheological properties of a sample, an oscillation system containing the sample is caused to perform free oscillations, and the damping caused by the sample is determined, the rheological properties of the sample being possible to determine by means of the damping. By this method, rheological properties can be determined for samples of a small volume and/or low viscosity. The method is especially adapted to measure body fluids. A rheometer for carrying out the method is also disclosed.

21 Claims, 3 Drawing Sheets

METHOD FOR MEASURING RHEOLOGICAL PROPERTIES AND RHEOMETER FOR CARRYING OUT THE METHOD

The present invention relates to a method of measuring rheological properties of a sample, and a rheometer for carrying out the method.

In medicine, rheology is a little used branch of science. The only exception is the measuring of the blood sedimentation reaction which for many years has been carried out to a large extent in order to check whether a person is sound. The blood sedimentation reaction is connected to the viscosity of the blood.

However, it is known that the viscosity of other body fluids may also be affected by a person's state of health. One knows, for example, that changes in the viscosity of the bile mirrors various states of ill-health in the liver and the biliary passages. Moreover, there is a strong connection between the function of the mucus in the bronchi and the elasticity of the mucus. A further example is that cardiac infarction is associated with an increase of the whole-blood viscosity.

It would thus be of interest if one could study in a simple manner the viscosity of different body fluids, such as blood, saliva, bronchial mucus, bile, semen, vaginal secretion, lachrymal fluid, synovial fluid and peritoneal fluid. However, today no apparatus is available for quick and simple registration of the viscosity of body fluids.

When measuring the blood sedimentation reaction, the sedimentation rate of the red blood corpuscles is determined by filling a test tube with blood and then allowing it to stand for about 1 h, whereupon the height of the plasma column above the blood corpuscles is measured. This measuring process is slow and cannot be used for other body fluids.

In industries, it is known to determine the viscosity of liquids by means of rotary rheometers.

A prior art, Couette-type rotary rheometer comprises two cylinders of slightly different diameters, one arranged in the other. The outer cylinder can be rotated by means of a drive, and the inner is stationary. The liquid sample whose viscosity should be determined is placed in the gap between the cylinders. The viscosity of the liquid sample is determined by measuring the moment by which the liquid affects the inner cylinder as the outer cylinder is rotated and the liquid is shorn between the cylinders.

For a number of reasons, such a rheometer is however not suited for use with body fluids since the volume of the fluid sample must be at least 10 ml to produce accurate viscosity values. Some body fluids, e.g. synovial fluid, has a total volume in the body of this magnitude, and therefore samples cannot be taken that are sufficient for the determination of viscosity.

Furthermore, some body fluids are of very low viscosity, in fact close to that of water. The viscosity of such fluids cannot be measured by means of the prior art rheometer since the effect of the fluid sample on the stationary cylinder is too small to be measured.

Finally, the prior art rheometer is far too expensive to make extensive use in medical attendance realistic.

One object of the invention therefore is to provide a method and a rheometer for measuring rheological properties of a fluid, which makes it possible to determine the viscosity of low viscosity fluids and/or small volumes of fluid samples.

A further object of the invention is to provide a method and a device which can replace the traditional measuring of the blood sedimentation reaction.

These objects are achieved by means of a method and a device having the characteristic features stated in the accompanying claims.

By causing an oscillation system containing the sample to perform free oscillations and by measuring the damping of the oscillation, which is caused by the sample, rheological properties of the sample can be determined. This principle can be generally used independently of the volume and viscosity of the sample. The method according to the invention can thus be used as an alternative to the known method described above.

The theory behind the invention is the following. Now assuming that a hollow cylinder whose inner radius is R and whose inner height is H is suspended by a torsion wire along its axis. The spring constant of this construction is $I\omega_0^2$, wherein I is the moment of inertia and $\omega_0$ the angular velocity as the oscillation system with the empty cylinder performs free torsional oscillations. The free torsional oscillations are damped owing to the damping in the torsion wire and the other suspension means. The damping is defined by the logarithmic decrement $\Delta$:

$$\Delta = 1/n \, (ln(A_n/A_1)),$$

wherein n is the number of periods of the oscillation, and $A_n$ is the amplitude of the oscillation in the nth period and $A_1$ is the amplitude in the first period of oscillation.

If the cylinder is filled with fluid and the oscillation system is caused to perform free torsional oscillations, the damping of the oscillation will be greater than in the case of an empty cylinder. As the cylinder oscillates, the oscillation will penetrate into the fluid in the cylinder. The penetration depth $\delta$ is determined by the viscosity $\eta$, the density of the fluid $\rho$, and the angular velocity $\omega$ according to the formula $$\delta = (\eta/\rho\omega)^{1/2}$$

By selecting a suitable oscillation frequency, a penetration depth $\delta$ of a low viscosity fluid can be obtained, which is much smaller than the radius R of the cylinder. In this case, the fluid in the centre of the cylinder will be immovable during the torsional oscillations and the fluid between the cylinder wall and the immovable portion of the fluid will be shorn. The shearing action promotes the damping of the oscillation. The damping caused by the shearing action can be measured, and on the basis of the damping the viscosity of the fluid can be determined.

For a viscous fluid the following relationship applies, provided that the penetration depth $\delta$ is much smaller than the radius R and the height H:

$$\eta = 2k\omega\rho(\Delta_v - \Delta_0)^2 \qquad (1)$$

wherein $\Delta_v$ and $\Delta_0$ are the logarithmic decrement in oscillation with and without fluid in the cylinder, and k is a calibration constant.

By measuring the damping and the relative frequency shift, the dynamic viscosity $\eta'$ and the storage modulus $G'$ can be determined for a slightly elastic sample according to the following formulae:

$$\eta' = 2k\omega\rho \, (\Delta_v - \Delta_0)\left(-\frac{\Delta\omega}{\omega_0}\right) \qquad (2)$$

and $$G' = k\omega^2\rho\left[(\Delta_v - \Delta_0)^2 - \left(\frac{\Delta\omega}{\omega_0}\right)^2\right] \qquad (3)$$

wherein $\left(-\dfrac{\Delta\omega}{\omega_0}\right)$ is the relative frequency shift.

If the penetration depth is not much smaller than the radius R and the height H, the formulae (1)–(3) are not valid. For determining the rheological properties of a sample in this case, the cylinder is replaced by e.g. a plate on which the sample is arranged, and a fixed abutment is caused to contact the sample, whereby the sample is shorn between the plate and the abutment as the oscillation system performs free oscillations. The presence of the sample in the oscillation system generally results in a damping of the oscillation which, like before, is represented by a logarithmic decrement $\Delta$, and a shift of the oscillation frequency from $\omega_0$ to $\omega$. By measuring the damping and the frequency, the dynamic viscosity $\eta'$ and the storage modulus G' can be determined according to the following formulae:

$$\eta = k_1(\Delta_V - \Delta_0) \qquad (4)$$

and, in a first approximation, $$G' = k_2(\omega^2 - \omega_0^2) \qquad (5)$$

wherein $k_1$ and $k_2$ are calibration constants.

The present invention makes it possible to determine rheological properties of samples having a small volume, since also small samples cause damping. To allow measuring of the damping in a reasonable time, the mass of the sample should preferably be an essential part of the oscillating mass in the rheometer.

The present invention further renders it possible to determine rheological properties of low viscosity samples. This is possible since the rheometer according to the invention has an insignificant self-damping as compared to the damping caused by the low viscosity sample. As an example, it may be mentioned that the self-damping is about 1% of the damping obtained when measuring a water sample.

The invention thus is well suited for use in determining the viscosity of blood and other body fluids.

Since a rheometer according to the invention is considerably less expensive to manufacture than prior art rheometers, the use of such a rheometer for determining the viscosity of blood could replace the traditional determining of the blood sedimentation reaction. In this case, the rheometer could be fitted with means for converting the viscosity values into blood sedimentation reaction values.

In the description of the theory behind the invention, the measuring cell, i.e. the cylinder, was suspended by a torsion wire, and the oscillation system performed free torsional oscillations. However, it will appreciated that the free oscillations need not be torsional oscillations, but that the corresponding damping is also obtained in e.g. pendulum oscillations.

The invention may be used to determine rheological properties of materials having viscous and/or elastic properties. The materials can be solid, liquid, gaseous, plastic or gel-like.

Figure 2:
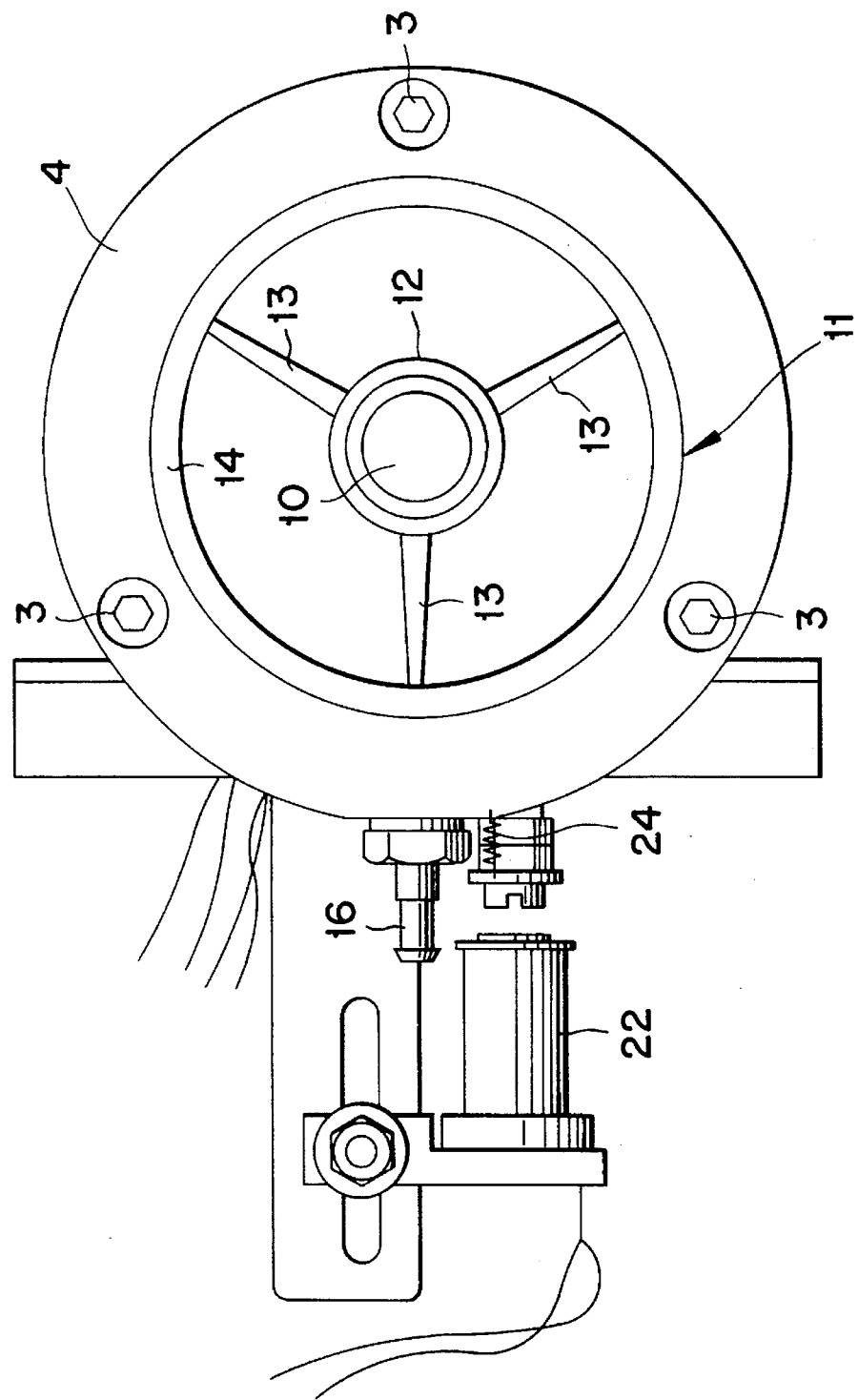
Figure 3:
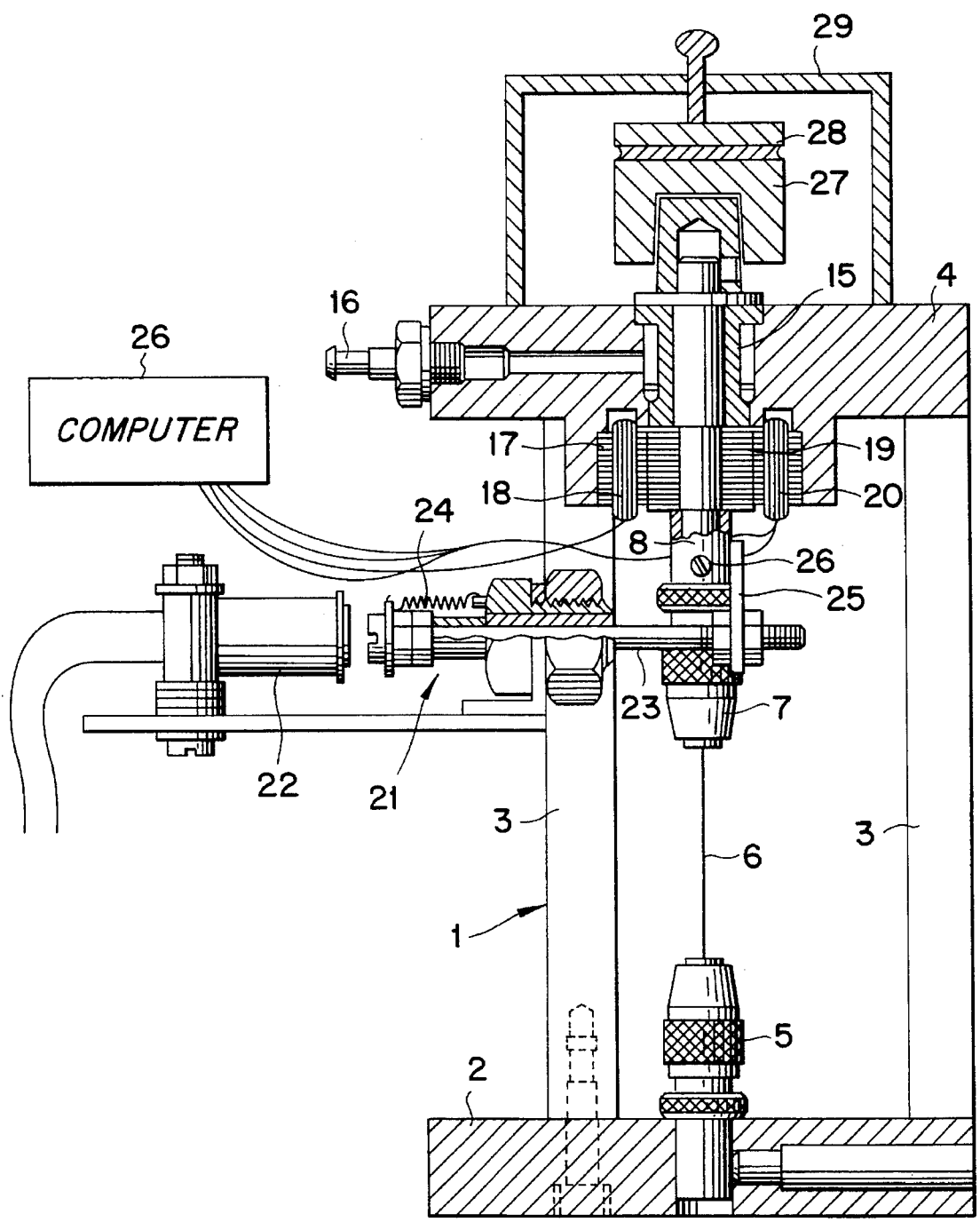

In the following, the method and the device according to the invention will be described by means of an embodiment, reference being made to the accompanying drawings in which FIG. 1 is a part-sectional side view of an embodiment of a device according to the invention;

FIG. 2 is a top plan view of an embodiment of a device according to the invention; and FIG. 3 is a part-sectional side view of a second embodiment of a device according to the invention.

FIG. 1 illustrates an embodiment of a rheometer according to the invention, which is adapted to measure samples having mainly viscous properties, especially low viscosity fluids. The rheometer comprises a stationary stand 1 having a bottom plate 2, three vertical legs 3 and an upper plate 4. A lower chuck 5 is attached to the bottom plate, and a torsion wire 6 is fixedly fastened to the lower end of the chuck. Torsion wires are commercially available and can be supplied with different spring constants. The upper end of the torsion ware 6 is attached to an upper chuck 7 which is connected in axial direction to a free shaft 8 which via a coupling 9 is connected to a mounting 10 in the shape of a truncated cone. A measuring cell 11 is detachably arranged on the mounting. As shown in more detail in FIG. 2, the measuring cell 11 comprises a tubular hub portion 12 from which three supporting arms 13 extend. At the ends facing away from the hub portion, the supporting arms 13 support a circular tube 14 which is adapted to contain a fluid sample. The tube 14 is circular in cross-section, and fluid can move freely in the tube without being obstructed by partitions or like obstacles while the boundary surfaces of the tube 14 are immovable relative to each other, the boundary surfaces constitute the only boundary surfaces with which the sample is in contact during the oscillations. As an alternative to the measuring cell with the tubular sample space, a cylindrical or plate-shaped measuring cell could be used. The main thing is that the measuring cell is rotationally symmetrical, and that the fluid can circulate in the sample space without being obstructed.

The free shaft 8 is mounted in an air bearing 15 in the upper plate 4 of the stand. The air bearing 15 essentially consists of a porous carbon bearing, which is arranged with a gap round the free shaft 8. Compressed air is supplied to an outlet 16 and is injected through the carbon bearing and into the gap, the shaft being fixed with insignificant damping of the oscillations. Air bearings are commercially available as "Porous Carbon Air Bearings".

A detector unit 17 for detecting the amplitude and frequency of the free oscillation is arranged between the upper chuck 7 and the air bearing 15. The detector unit is a so-called RVDT-unit (Rotational Variable Differential Transformer) which is commercially available. It comprises a primary winding 18, an armature 19 arranged on the free shaft 8, and two secondary windings 20 which are symmetrically arranged in angular direction relative to the primary winding. The RVDT-unit 17 is connected to a signal processing and calculating unit (computer 26).

The rheometer is further fitted with oscillation excitation means 21 comprising an electromagnet 22 which is fixedly mounted on the stand 1, a first bar 23 which is movably mounted on the stand and biassed in a resting position by means of a spring 24, a second bar 25 mounted on the first bar 23, and a pin 26 arranged on the free shaft 8. When voltage is applied to the electromagnet, the first bar 23 and the second bar 25 arranged thereon are pulled towards the electromagnet 22, the second bar 25 knocking into the pin 26 which causes the torsion wire 6, the free shaft 8, the mounting 10 and the measuring cell 11 to oscillate. As soon as the voltage to the electro-magnet is disconnected, the bar 23 returns to its resting position.

Alternatively, the RVDT-unit 17 may be used as excitation means, voltage being applied to one of the secondary windings for a short period of time.

The essential thing about the excitation is that it is performed in the same way on each occasion.

The function of the rheometer will now be described. Before being used, the rheometer is suitably calibrated for measuring a special fluid whose rheological properties are known or have been measured before by some other method. In the measuring operation, the measuring cell is filled with a fluid sample, and the oscillation is excited by the excitation means 21. The damping of the oscillation is measured by means of the RVDT-unit 17, a sinusoidal AC voltage of about 5 kHz is applied to the primary winding 19, and the differential signal from the secondary windings 20, which arises owing to the unsymmetrical position of the armature in relation to the secondary windings 20 during oscillation, is measured. The differential signal is demodulated by being sampled synchronously with the AC voltage applied to the primary winding in such a manner that a sample is taken in the same point in each period. The root mean square value of the demodulated signal is then converted into a DC voltage signal which thus represents the oscillation amplitude. This DC voltage signal is A/D-converted and supplied to a personal computer which calculates the viscosity as follows. At a first and a second predetermined level of the DC voltage, the number of samples is determined which has been taken until the DC voltage has decreased to the current level. Since the sampling frequency is known, the time it takes for the oscillation to be damped from the first to the second predetermined level can be determined by means of the number of samples taken. Knowing the oscillation frequency, the logarithmic decrement for the fluid sample can then be determined and, consequently, also the viscosity according to formula (1) on page 4.

The oscillation frequency can also be determined by means of the RVDT-unit 17 and, thus, also the relative frequency shift and the dynamic viscosity η' and the storage modulus G' according to formulae (2) and (3) on page 4.

In an embodiment of the rheometer which is intended for samples of higher viscosity or having more pronouncedly plastic or elastic properties, the shown tubular measuring cell 11 is replaced by a plate-shaped measuring cell, and an abutment is arranged on the rheometer so that the sample is shorn between the plate and the abutment. The abutment can be fixed on the rheometer. Thus, the measuring cell comprises boundary surfaces 27 and 28 for the sample which are movable relative to each other, one surface being fixed by means 29 and the other movable such that the sample is shorn between these surfaces during the oscillations, as shown in FIG. 3.

What is claimed is:

1. A method of measuring rheological properties of a sample, comprising the steps of:
   performing free oscillations of an oscillation system containing the sample,
   determining a damping of the oscillation, which is caused by the sample,
   measuring a frequency shift of the oscillations, which is caused by the sample, and
   determining rheological properties including viscosity and elasticity of the sample by means of the damping and the frequency shift.

2. The method as claimed in claim 1, wherein the oscillations are torsional oscillations.

3. The method as claimed in claim 2, further comprising the steps of exciting the oscillations in such a manner that the oscillations penetrate part-way into the sample, and that a portion of the sample is immovable during the oscillations.

4. A method of measuring rheological properties of a sample, comprising the steps of:
   performing free oscillations of an oscillation system containing the sample, including exciting the oscillations in such a manner that the oscillations penetrate part-way into the sample, and that a portion of the sample is immovable during the oscillations,
   determining a damping of the oscillation, which is caused by the sample, and
   determining rheological properties of the sample by means of the damping.

5. A rheometer for measuring rheological properties of a sample, comprising:
   an oscillation system including
      a measuring cell for holding a sample, wherein the measuring cell comprises boundary surfaces for the sample which are movable relative to each other, one surface being fixed and the other movable such that the sample is shorn between these surfaces during the oscillations, and
      an oscillation element to which the measuring cell is connected and by means of which the oscillation system can be caused to perform free oscillations, and
   a detector for detecting the amplitude of the oscillations.

6. The rheometer as claimed in claim 5, wherein a volume of the measuring cell is such that the mass of the fluid sample is a substantial part of the oscillating mass in the oscillation system.

7. The rheometer as claimed in claim 5, wherein the measuring cell is detachably mounted.

8. The rheometer as claimed in claim 5, wherein the oscillation element extends in a vertical direction.

9. The rheometer as claimed in claim 5, further including means for measuring the frequency of the oscillation.

10. The rheometer as claimed in claims 5, wherein the measuring cell is closed.

11. The rheometer as claimed in claim 5, wherein the rheometer is adapted to be used for measuring rheological properties of body fluids.

12. The rheometer as claimed in claim 11, wherein the rheometer is adapted to be used for measuring the viscosity of blood.

13. A rheometer for measuring rheological properties of a sample, comprising:
   an oscillation system including
      a measuring cell for holding a sample,
      an oscillation element to which the measuring cell is connected and by means of which the oscillation system can be caused to perform free oscillations, wherein the measuring cell is arranged on a mounting element which is connected to the oscillation element, and
      an air bearing in which the mounting element is mounted, and
   a detector for detecting the amplitude of the oscillations.

14. The rheometer as claimed in claim 13, further including means for measuring the frequency of the oscillation.

15. The rheometer as claimed in claim 13, wherein the rheometer is adapted to be used for measuring rheological properties of body fluids.

16. The rheometer as claimed in claim 15, wherein the rheometer is adapted to be used for measuring the viscosity of blood.

17. A rheometer for measuring rheological properties of a sample, comprising:
   an oscillation system including
      a measuring cell for holding a sample, wherein the measuring cell comprises boundary surfaces for the sample which are immovable relative to each other and which constitute the only boundary surfaces with which the sample is in contact during the oscillations, the measuring cell having dimensions such that the oscillations penetrate part-way into the sample, and that a portion of the sample is immovable during the oscillations, and an oscillation element to which the measuring cell is connected and by means of which the oscillation system can be caused to perform free oscillations, and a detector for detecting the amplitude of the oscillations.

18. The rheometer as claimed in claim 17, further including means for measuring the frequency of the oscillation.

19. The rheometer as claimed in claim 17, wherein the rheometer is adapted to be used for measuring rheological properties of body fluids.

20. The rheometer as claimed in claim 19, wherein the rheometer is adapted to be used for measuring the viscosity of blood.

21. A rheometer for measuring the viscosity of blood, comprising:

an oscillation system including a measuring cell for holding a sample, and an oscillation element to which the measuring cell is connected and by means of which the oscillation system can be caused to perform free oscillations, and a detector for detecting the amplitude of the oscillations as a measure of viscosity values, and means for converting viscosity values into blood sedimentation reaction values.

* * * * *